ically) US005296239A

United States Patent [19]

Colery et al.

[11] Patent Number: 5,296,239
[45] Date of Patent: Mar. 22, 1994

[54] PERACETIC ACID COMPOSITIONS AND PROCESS FOR OBTAINING THESE COMPOSITIONS

[75] Inventors: Jean-Claude Colery, Chaumont-Gistoux; Pierre Ledoux, Brussels, both of Belgium

[73] Assignee: Interox, Brussels, Belgium

[21] Appl. No.: 865,801

[22] Filed: Mar. 25, 1992

Related U.S. Application Data

[63] Continuation of Ser. No. 592,594, Oct. 4, 1990, abandoned.

[30] Foreign Application Priority Data

Oct. 5, 1989 [BE] Belgium ............................... 08901066

[51] Int. Cl.$^5$ ........................ A01N 39/00; A62D 3/00
[52] U.S. Cl. ............................... 424/613; 252/186.26; 252/186.28; 252/174.24; 252/174.21; 514/557
[58] Field of Search ............... 514/557; 252/186.26, 252/186.28, 174.24, 174.21; 424/613

[56] References Cited

U.S. PATENT DOCUMENTS

| 4,879,057 | 11/1989 | Dankowski et al. | 252/186.26 |
| 5,004,557 | 4/1991 | Nagarajan et al. | 252/174.24 |
| 5,118,436 | 6/1992 | Aoyagi et al. | 252/174.21 |

FOREIGN PATENT DOCUMENTS

| 0103416 | 3/1984 | European Pat. Off. | 252/186.26 |
| 0212976 | 4/1987 | European Pat. Off. | 252/186.26 |
| 0256443 | 2/1988 | European Pat. Off. | 252/186.26 |
| 1119841 | 12/1961 | Fed. Rep. of Germany | 252/186.26 |
| 906971 | 9/1962 | United Kingdom . | |

OTHER PUBLICATIONS

European Search Report dated Jun. 20, 1990.

*Primary Examiner*—Thurman K. Page
*Assistant Examiner*—Peter F. Kulkosky
*Attorney, Agent, or Firm*—Willian Brinks Hofer Gilson & Lione

[57] ABSTRACT

Peracetic acid compositions containing at least one thickening agent and optionally a stabilizer chosen from sequestering agents, free-radical scavengers and mixtures containing two or more of these products.

The preferred compositions are obtained by successively incorporating at least one stabilizer and then at least one thickening agent.

These compositions are especially capable of being employed for the disinfection of large bulks which are difficult to immerse and of nonhorizontal surfaces, and for detergency or bleaching at low temperature.

35 Claims, No Drawings

PERACETIC ACID COMPOSITIONS AND PROCESS FOR OBTAINING THESE COMPOSITIONS

This is a continuation application of application Ser. No. 07/592,594 filed Oct. 4, 1990, now abandoned.

The present invention relates to peracetic acid compositions.

Peracetic acid is a peroxide compound which is capable of applications similar to those of hydrogen peroxide, especially as bleaching, disinfecting or sterilizing agent, through a release of active oxygen.

Peracetic acid is found to be even more active than hydrogen peroxide, particularly at low temperature, and this makes its use especially advantageous in some disinfection, detergency or bleaching applications.

However, its use is made difficult in some cases because of its excessive fluidity, comparable to that of water. This is especially so in oxidizing and bactericidal treatments of nonhorizontal surfaces or of large bulks which are difficult to immerse in a vessel.

To widen its field of application, it therefore appears desirable to have the ability to present it in a form which permits especially a localized application with a limited fluid flow, and which offers a sufficient stability in storage and in handling.

Another disadvantage of peracetic acid results from the fact that it is capable of changing back into acetic acid and hydrogen peroxide in the presence of water. This phenomenon, already present in storage, is particularly prominent when it is diluted.

To maintain the advantages which stem from the choice of peracetic acid rather than hydrogen peroxide it is therefore important that the rate of reversion should be as low as possible in storage and in handling.

Finally, when peracetic acid is stored and handled there is a risk of a decrease in its active oxygen content.

The objective of the present invention is to provide peracetic acid compositions which are relatively nonfluid, are stable in storage and in handling and which are in a sufficiently homogeneous form to avoid differences in consistency and separation phenomena.

To this end, the invention relates to peracetic acid compositions which contain at least one thickening agent.

Various thickening agents can be employed for this purpose. They are generally chosen from the polymers and copolymers of acrylic monomers, their derivatives and mixtures containing two or more of these products. In particular, acrylic acid polymers and copolymers and their derivatives can be chosen to advantage. Their polymerization can be carried in situ or beforehand. Good results are obtained with polymers prepared beforehand.

The best results have been obtained with crosslinked acrylic acid polymers. Various polysaccharide derivatives can be employed usefully as crosslinking agents. In particular, sucrose or pentaerythritol which are substituted by a number of allyl groups can be advantageously chosen.

In practice, excellent results are obtained with an acrylic acid polymer crosslinked with a polyallylsucrose, marketed by the company B.F. Goodrich Chemical under the trademark Carbopol 934.

The thickened compositions according to the invention are generally not neutralized.

In general, compositions according to the invention contain at least 0.05% by weight of one or more thickening agents. In most cases this concentration does not exceed 10%. The preferred contents run from 0.1 to 6% by weight of one or more thickening agents.

In practice the compositions containing a thickening agent according to the invention generally have a fluidity which is characterized by a Matthis value not exceeding 25 cm/10 s. The compositions may optionally be in gelled form. They may have a Matthis value equal to 0 cm/10 s.

The Matthis value is measured using the flow meter of the same name, the use of which has been found particularly convenient in this case. The Matthis flow meter consists of a graduated rule comprising, at one of its ends, a cavity in the shape of a spherical cap 5.2 mm in depth, the radius of the sphere being 8 mm. A graduated groove starts 5 mm below the edge of the cavity to reach 15 mm further its definitive depth of 2.6 mm. This groove has a U-shaped profile. With the rule horizontal, the cavity is filled with the fluid being studied and the convex meniscus which has formed is removed from the cap merely by raking it off. The apparatus is then set vertically upright and the distance travelled by the fluid is read off after 10 seconds.

From a practical standpoint it is desirable that the thickened compositions according to the invention should also be stabilized.

Stabilized compositions mean compositions whose thickened form and active oxygen content are essentially maintained at the end of a long-term storage at room temperature.

In general, the thickened compositions according to the invention additionally contain at least one stabilizer. Various stabilizers can be employed. In most cases they are chosen from sequestering agents, freeradical scavengers and mixtures containing two or more of these products.

Many known sequestering agents can be employed for stabilizing the thickened compositions according to the invention. In general they can be chosen from nitrogenous carboxylic acids, hydroxyaminocarboxylic, hydroxycarboxylic or phosphonic acids, their derivatives and mixtures containing two or more of these products.

Various nitrogenous carboxylic acids or their derivatives can be usefully employed. Nitrogeneous carboxylic acids are intended to denote aminocarboxylic acids and carboxylic acids containing a nitrogeneous heterocyclic ring in their structure. In particular, good results are obtained with dipicolinic acid.

Various hydroxyaminocarboxylic acids or their derivatives can be usefully employed. In particular, 1,3-diamino-2-hydroxypropanetetracetic acid can be chosen to advantage.

Various hydroxycarboxylic acid acids or their derivatives can be usefully employed. In particular, sodium poly-alpha-hydroxyacrylate (Luxembourg patent 74,434, Solvay & Cie) or the agents mentioned in Federal German patent applications 1,904,940, 1,904,941 and 1,942,556 by Haschke can be advantageously chosen.

Phosphonic acids and their derivatives also yield very good results. Among these, alkylidenepolyphosphonic acids and/or polyalkylenephosphonic acids or their derivatives are advantageously chosen. In particular, it is possible to employ hexamethylenediamnetetra(-methylenephosphonic), diethylenetriaminepenta(methylenephosphonic), triethylenetetraminehexa(methylenephosphonic), tetraethylenepentaminehepta(methylenephosphonic) and pentaethylenehexamineocta(methylenephosphonic) acids or their derivatives. In practice, excellent results are obtained with diethylenetriaminepenta(methylenephosphonic) acid.

In most cases the sequestering agents are chosen from phosphonic acids, nitrogenous carboxylic acids, their derivatives and mixtures containing two or more of these products.

Many known free-radical scavengers can also be employed to stabilize the thickened compositions according to the invention. In general, they can be chosen from phenolic compounds and their mixtures. Among these, alkylhydroxybenzenes and more particularly butylhydroxytoluenes are advantageously adopted. In practice, good results are obtained with 2,6- or 3,5-bis-tert-butyl-4-methylphenol.

To guarantee the stability of the thickened peracetic acid compositions, care is taken that they should be substantially free from chlorides. This means that their chloride content does not exceed 5 and preferably 2 mg (of chlorine ions) per kg of composition. To do this, care is taken that the quantity of stabilizer and its chloride content should be such that these limits are not exceeded.

It is frequently advantageous to employ a number of the proposed stabilizers simultaneously. At least one sequestering agent and a free-radical scavenger are preferably incorporated.

The compositions according to the invention may additionally contain one or more other stabilizers as well as one or more other thickening agents.

The invention relates to any grade of peracetic acid. In general, peracetic acid takes the form of solution and, besides peracetic acid, these solutions contain especially acetic acid, hydrogen peroxide and water in various proportions which are a function of their equilibrium state and of their subsequent use.

In general the compositions according to the invention are characterized by a weight concentration of peracetic acid which does not go down below 1%. In most cases work is done with peracetic acid weight concentrations not exceeding 40% of the composition.

In general the compositions according to the invention have an active oxygen content of at least 0.1% by weight. In most cases this content does not exceed 20%.

Furthermore, compositions according to the invention generally contain at least 0.005% by weight of one or more stabilizers. In most cases this concentration does not exceed 5%.

In particular, the compositions according to the invention advantageously contain at least 0.005% by weight of one or more sequestering agents. This concentration preferably does not exceed 5%. Similarly, the compositions according to the invention advantageously contain at least 0.0005% by weight of one or more freeradical scavengers. This concentration preferably does not exceed 0.05%.

The respective concentrations of thickening agent and of stabilizer are chosen and can be adapted, especially as a function of the peroxide content of the composition, of its pH, of the temperature and of the dilution when used.

The compositions according to the invention can be prepared by various processes.

The present invention also relates to a process for obtaining thickened and stabilized peracetic acid compositions, according to which at least one stabilizer chosen from sequestering agents, free-radical scavengers and mixtures containing two or more of these products, followed by at least one thickening agent, are successively incorporated into a solution of peracetic acid.

In practice, in a first stage, the stabilizer(s) is (are) incorporated into the solution of peracetic acid while advantageously maintaining a moderate stirring which ensures a sufficient turbulence and improves the homogeneity of the mixture. Next, while the thickening agent(s) is (are) being added, it is preferable to increase the stirring gradually in order to maintain a vortex despite the thickening of the composition.

The process according to the invention offers the advantage of providing thickened and stabilized compositions merely by mixing at room temperature, without any heat or other treatment being required. The incorporation of the stabilizer(s) before thickening makes it easier to homogenize the mixture without compromising the subsequent stability.

The present invention provides thickened compositions which are remarkably stable, especially owing to the choice and the combination of the thickening agents and stabilizers. They can retain their essential active oxygen content and viscosity characteristics at the end of a long-term storage at room temperature. By virtue of their properties they are particularly suitable for use in bleaching or disinfection of large bulks which are difficult to immerse in a vessel, for bactericidal treatment of nonhorizontal surfaces especially in a hospital or industrial environment and for detergency or bleaching at low temperature.

The nonlimiting examples given below are intended to illustrate the invention without restricting its scope.

In all the examples the initial solution is a solution containing, by weight, 15% of peracetic acid, 14% of hydrogen peroxide, approximately 28% of acetic acid and approximately 43% of water, to which has been added 1% of a solution (of approximately 60% strength) of 1-hydroxyethylidene-1,1-diphosphonic acid of trademark Dequest 2010. This initial solution has a total active oxygen content of approximately 98 g/kg.

In the examples the fluidity of the composition was measured using a Matthis flow meter.

EXAMPLE 1

This example refers to a starting solution diluted in order to obtain an active oxygen content of 25 g/kg.

400 ml of this dilute solution were placed in a narrow beaker. To thicken the solution, without adding stabilizers, 3.5% by weight of polyacrylic acid crosslinked with a polyallylsucrose, in solid form, with a molecular weight approximately equal to 3,000,000, of trademark Carbopol 934, were incorporated. This introduction was performed slowly to avoid the formation of lumps, with a moderate turbulence maintained by a cross-bladed stirrer whose speed was increased as the thickening progressed.

The thickened solution was not neutralized.

The Matthis value obtained for the composition according to this example was less than 0.5 cm/10 s, clearly showing the result of the thickening according to the invention.

This composition was then stored for 12 weeks at a temperature of 25° C.

At this time, the Matthis value of the composition was 15 cm/10 s. A measurement of the total oxidizing power by titration with sodium thiosulphate (conventional iodometry) revealed a 19% loss of the active oxygen content (AVOX).

EXAMPLE 2

Two stabilizers according to the invention were added before thickening to a solution identical with that of Example 1.

To do this, 0.03% by weight of a solution containing 50% of diethylenetriaminepenta(methylenephosphonic) acid, of trademark Sequion 40H50), with a chloride content of less than 0.05 g per liter of solution, and 0.03% by weight of a free-radical scavenger, 2,6-di-tert-butyl-4-methylphenol, of trademark Ionol CP were incorporated, with turbulence being provided by a cross-bladed stirrer.

When the stabilizers had dissolved, thickening was carried out in the same way as in Example 1.

After manufacture, the composition had a Matthis value of less than 0.5 cm/10 s.

This composition was then stored, as in Example 1, for 12 weeks at a temperature of 25° C.

At this time the Matthis value of the composition was less than 0.5 cm/10 s and the decrease in oxidizing power was of 4% AVOX.

EXAMPLE 3

This example refers to the composition of Example 2, after 25 weeks' storage at a temperature of 25° C.

At this time the measured Matthis value was 4 cm/10 s and the decrease in oxidizing power was of 9% AVOX.

A comparative examination of the results of Examples 2 and 3 in relation to those of Example 1 illustrates the effectiveness of the combined incorporation of a sequestering agent and of a free-radical scavenger, both in relation to the maintenance of the thickened form and to that of the active oxygen content.

EXAMPLE 4

This example refers to a starting solution diluted in order to obtain an active oxygen content of 5 g/kg and then thickened in accordance with Example 1, without incorporation of stabilizer.

This composition was then stored for 28 weeks at a temperature of 35° C.

At this time it had recovered its perfectly fluid form (Matthis value greater than 30 cm/10 s).

EXAMPLE 5

Three stabilizers according to the invention were added before thickening to a solution identical with that of Example 4.

To do this, 0.005% by weight of a neutralized solution containing 25% in the form of diethylenetriaminepenta(methylenephosphonic) acid, of trademark Dequest 2066, with a chloride content of less than 5% by weight, 0.03% by weight of dipicolinic acid and 0.03% by weight of 2,6-di-tert-butyl-4-methylphenol, of trademark Ionol CP, were incorporated, with turbulence being provided by a cross-bladed stirrer.

This solution was then stored for 28 weeks at a temperature of 35° C.

At this time the Matthis value of the composition was 1 cm/10 s and the decrease in oxidizing power was of 3% AVOX.

A comparative examination of the results of Examples 4 and 5 illustrates the effectiveness of the combined incorporation of 3 stabilizers.

We claim:

1. Peracetic acid compositions comprising a solution of peracetic acid, at least one thickening agent selected from the group consisting of polymers of acrylic monomers, copolymers of acrylic monomers, derivatives of polymers of acrylic monomers, derivatives of copolymers of acrylic monomers and mixtures thereof, the amount of the thickening agent being such that the fluidity of the compositions does not exceed a Matthis value of 25 cm/10 s, said fluidity remaining substantially constant after a 12 week storage, and further comprising at least one stabilizer selected from the group consisting of sequestering agents, free-radical scavengers and mixtures thereof.

2. Compositions according to claim 1, wherein the thickening agent comprises a crosslinked acrylic acid polymer.

3. Compositions according to claim 1, comprising from 0.05 to 10% by weight of therefore thickening agents.

4. Compositions according to claim 1, wherein the sequestering agent is selected from the group consisting of phosphonic acids, nitrogenous carboxylic acids, their derivatives and mixtures thereof.

5. Compositions according to claim 1, wherein the stabilizer is the free-radical scavenger comprising at least one phenolic compound.

6. Compositions according to claim 1, comprising from 1 to 40% by weight of peracetic acid.

7. Compositions according to claim 1, comprising from 0.1 to 20% by weight of active oxygen and from 0.005 to 5% by weight of one or more stabilizers.

8. A process for obtaining the peracetic acid compositions according to claim 1, wherein at least one stabilizer selected from the group consisting of sequestering agents, free-radical scavengers and mixtures thereof, followed by at least one thickening agent, selected from the group consisting of polymers of acrylic monomers, copolymers of acrylic monomers, derivatives of polymers of acrylic monomers, derivatives of copolymers of acrylic monomers and mixture thereof, are consecutively incorporated into the solution of peracetic acid.

9. Compositions of claim 1, wherein the thickening agent comprises a crosslinked acrylic acid polymer.

10. Compositions of claim 1, wherein the stabilizer is the sequestering agent selected from the group consisting of phosphonic acids, nitrogenous carboxylic acids, hydroxyaminocarboxylic acids, hydroxycarboxylic acids, their derivatives and mixtures containing two or more of these products.

11. Compositions of claim 9, wherein the stabilizer is the free-radical scavenger comprising at least one phenolic compound.

12. Compositions of claim 11, wherein the phenolic compound is at lest one alkylhydroxybenzene compound.

13. Compositions of claim 12, wherein the phenolic compound is butylhydroxytoluene.

14. Compositions of claim 13, wherein the phenolic compound is 2,6-bis-tert-butyl-4-methylphenol or 3,5-bis-tert-butyl-4-methylphenol.

15. Compositions of claim 9, comprising from about 1 to about 40% by weight of peracetic acid.

16. Compositions of claim 1, comprising from about 1 to about 40% by weight of peracetic acid.

17. Compositions of claim 1, comprising from about 0.1 to about 20% by weight of active oxygen and from about 0.005 to about 5% by weight of the stabilizer.

18. Compositions of claim 16, comprising from about 0.1 to about 20% by weight of active oxygen and from about 0.005 to about 5% by weight of the stabilizer.

19. A method for producing a peracetic acid composition, having such fluidity that Matthis value of the composition is not greater than about 25 cm/10 s, comprising:
  about 0.05 to about 10% by weight of at least one thickening agent selected form the group consisting of polymers of acrylic monomers, copolymers of acrylic monomers, polymers of derivatives of acrylic acid, copolymers of derivatives of acrylic acid an mixtures thereof; and
  at least one stabilizer selected from the group consisting of sequestering agents, free-radical scavengers and mixtures thereof;
comprising initially adding to a solution of peracetic acid the stabilizer and, subsequently, adding to the solution the thickening agent, thereby producing the peracetic acid composition having a substantially constant fluidity after a 12 week storage.

20. A method of claim 19 wherein the solution of peracetic acid comprises an aqueous solution.

21. Compositions according to claim 5, characterized in that the phenolic compound is at least one alkylhydroxybenzene compound.

22. Compositions according to claim 21, characterized in that the alkylhydroxybenzene compound is butylhydroxytoluene.

23. Compositions according to claim 22, characterized in that the butylhydroxytoluene is 2,6-bis-tert-butyl-4-methylphenol or 3,5-bis-tert-butyl-4-methylphenol.

24. Compositions according to claim 1, characterized in that the sequestering agent is selected from the group consisting of phosphonic acids, nitrogenous carboxylic acids, hydroxyaminocarboxylic acids, hydroxycarboxylic acids, their derivatives and mixtures containing two or more of these products.

25. Compositions according to claim 1, which are substantially free of chlorides.

26. Compositions according to claim 1, comprising not more than 5 mg of chlorine ions per kg of the compositions.

27. Compositions according to claim 26, comprising not more than 2 mg of chlorine ions per kg of the compositions.

28. Compositions of claim 9, which is substantially free of chlorides.

29. Compositions of claim 9, comprising not more than 5 mg of chlorine ions per kg of the composition.

30. Compositions of claim 29, comprising not more than 5 mg of chlorine ions per kg of the composition.

31. A method of claim 19, wherein the peracetic acid composition is substantially free of chlorides.

32. A method of claim 19, wherein the peracetic acid composition comprises not more than 5 mg of chlorine ions per kg of the composition.

33. A method of claim 32, wherein the peracetic acid composition comprises not more than 2 mg of chlorine ions per kg of the composition.

34. Compositions according to claim 1, wherein the solution of peracetic acid comprises an aqueous solution.

35. Compositions of claim 9 wherein the solution of peracetic acid comprises an aqueous solution.

* * * * *

UNITED STATES PATENT AND TRADEMARK OFFICE
CERTIFICATE OF CORRECTION

PATENT NO. : 5,296,239

DATED : March 22, 1994

INVENTOR(S) : Jean-Claude Colery et al.

It is certified that error appears in the above-indentified patent and that said Letters Patent is hereby corrected as shown below:

Col. 2, line 67, change "hexamethylenediamnetetra" to --hexamethylenediaminetetra--

Col. 6, line 22, change "therefore" to --the--

Col. 6, line 48, chance "claim 1" to --claim 9--.

Col. 6, line 58, change "lest" to --least--.

Col. 8, line 22, change "5 mg" to --2 mg--.

Signed and Sealed this

Twenty-seventh Day of September, 1994

Attest:

BRUCE LEHMAN

Attesting Officer     Commissioner of Patents and Trademarks